United States Patent [19]

Christensen

[11] Patent Number: Plant 5,397

[45] Date of Patent: Jan. 29, 1985

[54] MINIATURE ROSE PLANT CV AROPRAWN

[75] Inventor: Jack E. Christensen, Ontario, Calif.

[73] Assignee: Armstrong Nurseries, Inc., Ontario, Calif.

[21] Appl. No.: 503,047

[22] Filed: Jun. 10, 1983

[51] Int. Cl.[3] ..... A01H 5/00

[52] U.S. Cl. ..... Plt./7

[58] Field of Search ..... Plt./7

*Primary Examiner*—Robert E. Bagwill

*Attorney, Agent, or Firm*—Synnestvedt & Lechner

[57] ABSTRACT

A rose plant of the hybrid miniature class, having a unique petal coloration of soft cream edged with a delicate purple cultivated primarily for garden decoration.

1 Drawing Figure

This invention relates to a hybrid miniature roseplant cv. Aroprawn. The plant is a dwarf bush outdoor seedling cultivated primarily for garden decoration.

The seed parent was "Foxy Lady" (U.S. Plant Pat. No. 4,762) and the pollen parent was "Deep Purple" (U.S. Plant Pat. No. 4,672). The plant was hybridized by Jack E. Christensen in Ontario, Calif., by crossing "Foxy Lady" and "Deep Purple." The descriptive and comparative references to this plant and its bloom hereinafter will relate to plants of the same class grown in this region. This variety preserves its distinguishing characteristics through succeeding propagations, by cuttings and budding.

This new variety is most readily distinguished from its seed parent, Foxy Lady (U.S. Plant Pat. No. 4,762), by the combination of the following characteristics. Whereas Foxy Lady produces flowers of a relatively uniform coral pink coloration, the new rose bears flowers of a cream coloration bordered with soft pink essentially as described and illustrated herein. The new variety produces a low bush, whereas Foxy Lady becomes significantly taller (almost twice as big as the Aroprawn rose plant in both height and breadth); nevertheless both are classified as miniature hybrids. Whereas Foxy Lady produces very ovoid, short buds, the buds of the new cultivar are proportionately longer and less ovoid. The Aroprawn rose plant produces abundant, moderately heavy foliage whereas the foliage of Foxy Lady has a significantly heavier and more leathery texture.

The new variety differs from its pollen parent, Deep Purple (U.S. Plant Pat. No. 4,672), most notably in the following respects. Whereas the new rose cv. Aroprawn bears flowers of a cream coloration bordered with soft pink, as described and illustrated herein, its pollen parent Deep Purple bears flowers of a relatively uniform deep purple-pink coloration. Deep Purple is classified as a floribunda and bears flowers of 2½ to 3½ inch diameter, the new seedling is classified as a miniature and bears significantly smaller flowers of a 1½ to 2 inch diameter. Whereas the new rose bears flowers of 20 to 25 petals, Deep Purple bears flowers of significantly higher petalage (32 to 40). Whereas the new rose has moderately heavy, semi-glossy small foliage, Deep Purple has significantly heavier, moderately large, leathery foliage with a glossy surface.

The accompanying drawing illustrates the plant in color and shows the flowering thereof from bud to full bloom.

Throughout this specification, color names beginning with a small letter signify that the name of that color, are used in common speech, is aptly descriptive. Color names beginning with a capital letter designate values based upon The R.H.S. Colour Chart, put out by The Royal Horticultural Society in London.

FLOWER

The flowers are consistently classically formed flowers produced in good proportion to the foliage and plant and are sometimes borne singly, but sometimes three to five or more to a stem in regular clusters well above the foliage on strong stems which are of medium length for the class. The plant blooms abundantly outdoors, and nearly continuously during the growing season. The blooms have a slight tea fragrance.

BUD

The peduncle is of average length for the class and of average caliper, erect, stiff and almost smooth, with a few stipitate glands.

Before the calyx breaks, the bud is of medium size for miniature roses, medium-length, pointed and ovoid, with few slender foliaceous appendages and few stipitate glands on the surface of the bud. Usually, slender foliaceous parts extend beyond the tip of the bud one-quarter or more of its length.

As the calyx breaks, the color is between Red 43C and Red 47B. The inner surface of the sepals carries a fine, wooly tomentum; margins are lined with stipitate glands and hairs.

As the first petal opens, the bud is average in size, of medium-length to long, pointed and ovoid to urn-shaped. On the outer surface of the petal, the base is near White 155A and gradually deepens to between Red 43D and Red 48B at the petal edge. The inside surface of the inner petal has a zone of near white 155A that covers about ½ to ⅓ of the lower and inner part of the petal—the remainder of the petal suffuses to between Red 43D and Red 48B. The bud opens up well, and is not prevented from opening by hot, wet or dry weather.

BLOOM

The size of the bloom when fully open is average to large, for miniature roses, being from 1½ inch to 2 inches in diameter. Petalage is double, with from 20 to 25 petals, plus 1 to 4 petaloids arranged regularly. The bloom is high centered at first, becoming open to cupped. At first the petals remain loosely cupped, with tips reflexed outward, becoming later, at maturity, less cupped, with tips reflexed outward.

PETALS

The petals are of medium thickness, the texture of the inside of the petal is slightly shiny to velvety and the outside satiny. The outside petals are round to broadly obovate with apex flat. Intermediate petals are obovate with a rounded apex. Inside petals are narrowly obovate with a rounded apex. The colors may be modified by being bordered or margined or penciled or shaded and/or washed or tinted with other colors.

The paragraph immediately following describes color values observed in a flower newly opened in the month of November. The plant has been grown outdoors, in Ontario, Calif.

The outer surfaces of all petals (outside, intermediate and inside) were all essentially the same in coloration, having a near White 155A zone covering the majority of the lower and central portions of the petal. Near the petal edge the color deepens to between Red 49B and Red 48C. The inner surfaces of all petals (outside, intermediate and inside) were all essentially the same in coloration. having a near White 155A zone covering about ½ to ⅔ of the lower and central portions of the petal and the remainder of the petal gradually deepening to between Red 49A and Red 48C at the petal edge.

The following paragraph describes color values observed in a flower which had been open for three days in the month of November. The plant had been grown outdoors, in Ontario, Calif.

The outer surface of both the outside petal and the inside petal have a zone of near White 155B that covers the majority of the lower and central portions of the petal. At the petal edge the color gradually suffuses to between Red 49C and Red 48D.

The general color effect of the newly opened flower is near White 155A in the central zone and each petal is broadly edged with between Red 49A and 48C. In a flower that had been three days open the central zone is near White 155B and with each petal less broadly edged with between Red 49C and Red 48D. The petal persists; fading to between Yellow-White 158D and White 155A. It is not particularly affected by hot, wet or dry weather.

The flower on the bush in the garden persists for from 3 to 4 days in the month of November. Cut roses grown outdoors and kept at living-room temperatures persist for from 4 to 5 days in the month of November.

REPRODUCTIVE ORGANS

The stamens are average to many in number and are arranged regularly but with a few tucked in the calyx.

The filaments are of short to medium-length for the class. Most are with anthers.

The anthers are of a medium size for the class, all opening approximately at the same time. The color when immature is near Yellow-Orange 17C and near Greyed-Orange 166A when mature.

There is an abundant amount of pollen which is near Yellow-Orange, 17D in color.

The pistils are approximately 65 in number, this being average for the class.

The styles are moderately uneven, short to average in length, thin to average in caliper, and bunched.

The stigma is near Red 45B in color.

The ovaries are usually all enclosed in the calyx.

This new variety does not naturally set hips in Ontario, Calif., and for that reason no sepals or seeds are described.

FOLIAGE

The compound leaves usually comprise 3 to 5 leaflets. They are abundant, of small to medium size for miniature roses, moderately heavy and semi-glossy. The leaflets are oval, with apex acute, base round and margin doubly serrate to dentate. The attractive semi-glossy foliage clothes even the lower branches.

The upper surface of the mature foliage is between Green 137A to darker than Yellow-Green 147A, in color. The under surface is near Greyed-Green 191A.

The young foliage is near Yellow-Green 146A and Green 137A, washed heavily with near Greyed-Purple 187A on its upper surface. The under surface is near Greyed-Purple 183B.

The rachis is light to average in size, grooved on its upper side, with some stipitate glands on the edges. The under side is moderately prickly and with stipitate glands.

The stipules are short to medium-length, medium-width, with medium-length points turning out at an angle of more than 45°.

The plant displays a more than average resistance to mildew and blackspot when compared to other commercialized varieties grown under comparable conditions in Ontario, Calif.

GROWTH

The plant is a dwarf variety of upright to spreading bushy habit producing a low, round, well-branched bush. Its growth is vigorous, with canes which are medium to heavy caliper for miniature roses.

The main stems are between Yellow Green 144B and Yellow-Green 146C in color. They bear very few large prickles which are of medium to long length, and hooked slightly downward, with a moderately short narrow base. The large prickles are near Greyed-Orange 177A, in color. There are no small prickles and no hairs.

The branches are between Yellow Green 144A and Yellow-Green 147A in color. They bear a few large prickles which are of medium to long length, hooked slightly downward, with a moderately short narrow base. These large prickles are near Greyed-Purple 183B in color. There are no small prickles and no hairs.

New shoots are between Yellow-Green 144A and Yellow-Green 147A in color and are washed heavily with near Greyed-Purple 183A. They bear from a few to several large prickles which are of medium to long length, hooked slightly downward, with a short to medium-length, moderately narrow base. The color of these large prickles is near Greyed-Purple 183A. There are no small prickles and no hairs.

I claim:

1. A new and distinct variety of rose plant of the hybrid miniature class, substantially as herein shown and described, and being especially characterized in that its consistently classically formed flowers are produced in good proportion to the foliage and plant; its abundant and nearly continual production of flowers borne both singly and in clusters, well above the foliage; its consistently low, round, well-branched bush; its attractive and abundant semi-glossy foliage clothes even the lower branches and in its unique petal coloration of soft cream edge with a delicate pink.

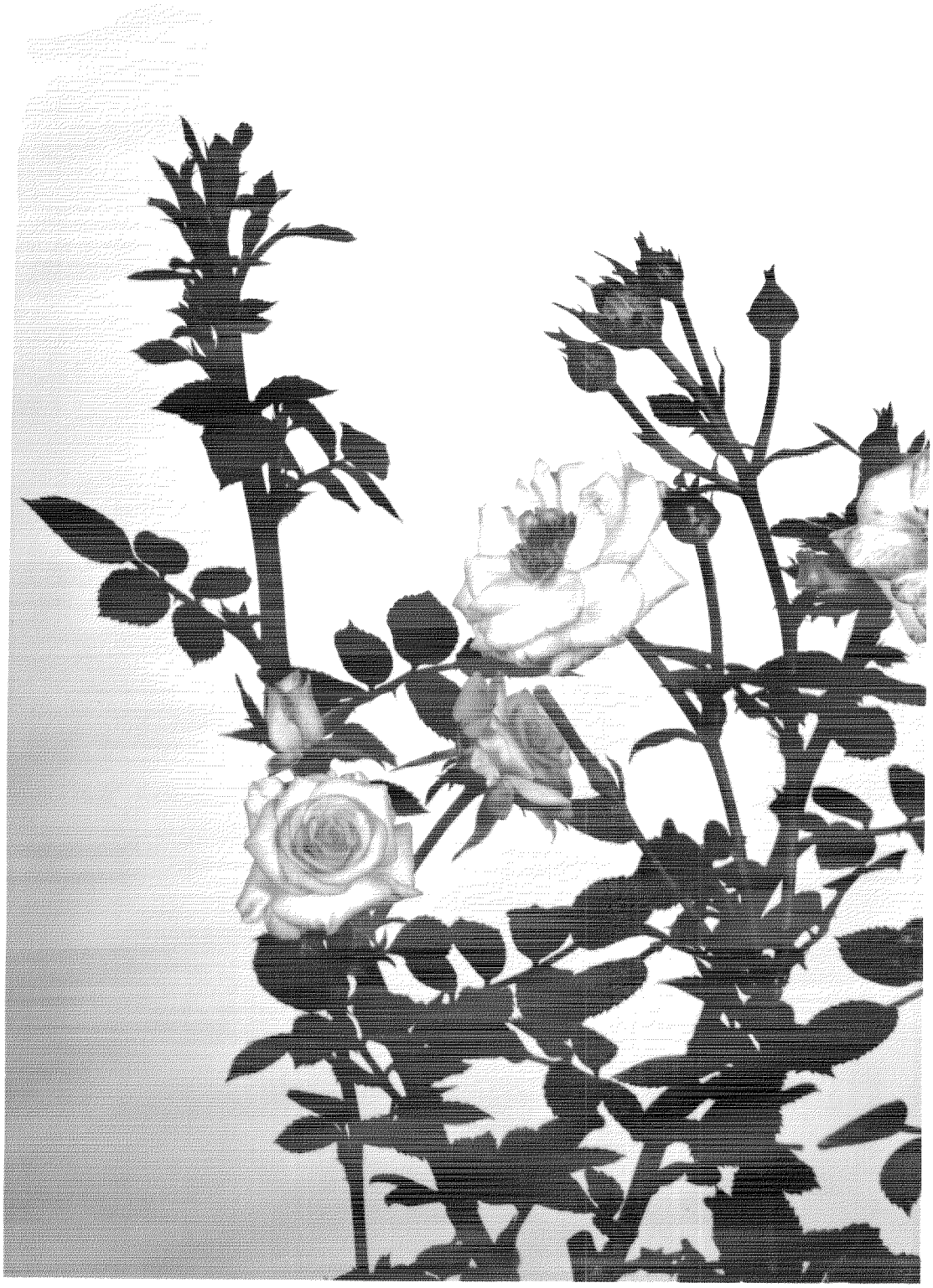

* * * * *